United States Patent [19]

Yamazaki et al.

[11] Patent Number: 5,531,992
[45] Date of Patent: Jul. 2, 1996

[54] LOW MOLECULAR WEIGHT VEGETABLE COMPOSITION

[75] Inventors: Hiroko Yamazaki, Koganei; Masahiro Kuroda, Toyonaka; Kozo Niwa, Kouchi, all of Japan

[73] Assignee: Kozo Niwa, Kouchi, Japan

[21] Appl. No.: 253,423

[22] Filed: Jun. 2, 1994

Related U.S. Application Data

[63] Continuation of Ser. No. 927,465, Aug. 10, 1992, abandoned.

[30] Foreign Application Priority Data

Aug. 14, 1991 [JP] Japan ................... 3-204207

[51] Int. Cl.$^6$ .................................... A61K 35/78
[52] U.S. Cl. ................... 424/195.1; 514/783; 514/825; 514/886; 435/170; 435/195; 435/200
[58] Field of Search .............. 424/195.1, 196.1; 514/783, 825, 886; 435/170, 200, 195

[56] References Cited

U.S. PATENT DOCUMENTS 4,871,763  10/1989  Goerler et al. ................... 514/452
5,009,891   4/1991  Niwa et al. ..................... 424/195.1
5,196,448   3/1993  Parry ............................ 514/452

FOREIGN PATENT DOCUMENTS 6485919   3/1989   Japan .
2258614   2/1993   United Kingdom .
  97285  12/1978   WIPO .
 148072  11/1989   WIPO .

OTHER PUBLICATIONS

Kalmar et al. *Agents Action*, 29 (3–4), pp. 239–246, (1990).

*Primary Examiner*—Douglas W. Robinson
*Assistant Examiner*—Howard C. Lee

[57] ABSTRACT

A low molecular weight vegetable composition comprising a seed of Milk Thistle which are heated with far infrared rays, for example, using a vessel comprising ceramics and then brewed with brewing bacteria such as "Koji" fungus, digestive enzyme, protein hydrolase or a precursor giving said enzyme or said protein hydrolase.

5 Claims, No Drawings

LOW MOLECULAR WEIGHT VEGETABLE COMPOSITION

This is a continuation of co-pending application Ser. No. 927,465 filed on Aug. 10, 1992, now abandoned.

BACKGROUND OF THE INVENTION

1. Field of the Invention

This Invention relates to a low molecular weight vegetable composition having anti-inflammatory effect.

2. Related Art Statement

Milk Thistle (Japanese name: Santorisoh; Scientific name: Silybum marianum, silybinin) is a plant of wild growth In the wildernesses of Canada, the northern U.S.A., and the nothern Europe, whose seed is a solid, long and slender rod shaped one having ivory-like gloss on the surface thereof. Conventional researches concerning the seed of Milk Thistle have reported that (1) flavonoids are contained with large amounts; (2) as shown from animal experimental results, It has potent antidotal activity and has a liver protective effect; (3) also as shown from animal experimental results, it promotes synthesis of RNA (Ribo Nucleic Acid) of liver; etc., but there has never been reported about anti-inflammatory effect thereof.

On the other hand, K. Niwa, Japanese Patent Application Laid-Open No. 63-79834, "Antioxidant Composition" (corresponding U.S. Pat. No. 5,009,891) provided a composition obtained by heating plant seeds such as rice, wheat, soybean, adzuki bean, sesame seed and "hatomugi" (pearl barley), or germs thereof with far infrared rays, then subjecting them to brewing treatment, and adding a vegetable oil obtained from a plant in the same manner, and showed that the composition thus-obtained has an active oxygen $(O\text{---}O^-)$ inhibiting activity (antioxidant activity). However, this composition hardly shows anti-inflammatory effect other than the antioxidant activity.

SUMMARY OF THE INVENTION

The present Inventors have made experiments relating to the effects of Milk Thistle seed to which specific treatment has been applied as mentioned hereinbelow and untreated Milk Thistle seed on human white blood cell, and have administered actually these Milk Thistle seeds orally to inflammatory patients, and have found that the treated seed of Milk Thistle shows remarkable anti-inflammatory effect, whereby having accomplished the present invention.

An object of the present invention is to provide an anti-inflammatory agent produced from seed of Milk Thistle.

Another object of the present invention is to provide a food additive produced from seed of Milk Thistle.

The low molecular weight vegetable composition of the present Invention can be obtained by processing seeds of Milk Thistle according to the following method.

First, seeds of Milk Thistle are heated by far infrared rays. More specifically, the seeds of Milk Thistle are heated using a vessel such as a pan and a pot coated at the Inner surface thereof with ceramics which irradiate far Infrared rays, preferably far infrared rays having a wavelength of 4 to 14 µm, i.e. so-called the raising rays, or a vessel such as a pottery produced of ceramic earth Irradiating far infrared rays, mixed with stones, gravel, sand etc. including metal oxides.

Heating is preferably carried out at a temperature near to 100° C. but not exceeding 100° C. while slowly stirring so as not to scorch the seeds. Incidentally, the source of the far Infrared rays to be used for heating is not limited only to the above vessel such as a pan, a pot and a pottery, but optional material may be used so long as it irradiates far infrared rays (preferably the raising rays having a wavelength of about 4 to 14 µm) such as platinum electromagnetic wave fiber. Heating time depends on the kind of the employed source of the far infrared rays and on the strength of the far infrared rays, although it is generally about half an hour to about 2 hours. In addition to usual heating, steaming may be employed as far as a vessel used is one which irradiates far infrared rays.

Next, heated seeds are subjected to brewing. More specifically, brewing is carried out by using brewing bacteria, such as "Koji" fungus (*Aspergillus oryzae*) at a temperature of 27° to 35° C. for 3 to 7 days.

For brewing, in addition to the brewing bacteria, there may be used, for example, (1) a substance which has brewing ability such as ripened papaya, fruit Juice of pineapple, skin of fig, skin of grape, bark of young bamboo, (2) digestive enzyme such as diastase, pancreatin, (3) protein hydrolase derived from microorganism, such as protease, pepsin, trypsin, and (4) a precursor giving the above digestive enzyme or protein hydrolase.

When the low molecular weight vegetable composition of the present invention is used as an anti-inflammatory agent, the material subjected to the above heating treatment with far infrared rays and brewing treatment is powdered, or prepared to be granule, tablet or capsule by the conventionally known methods and administered orally with a suitable dose. The composition of the present invention can be used in the range of 9–27 g/day as an anti-inflammatory agent.

Also, the above mentioned powder may be added to various kinds of foods or drinks to supply them as health foods.

In the seed of Milk Thistle, low molecular weight anti-inflammatory substances such as flavonoids, carotene, catechin, polyphenols, vitamin E and vitamin C are present in a mutually polymerized state, in other words, in the inactive state. Thus, even when the seed of Milk Thistle is taken orally without any treatment, not remarkable anti-inflammatory effect can be obtained.

That is, heating treatment by far infrared rays and brewing treatment thereafter cut molecular chain of the inactive type polymers to activate the low molecular weight anti-inflammatory substances.

However, even when heating treatment by far infrared rays and brewing treatment are carried out with respect to other plant seeds containing anti-inflammatory substances such as flavonoids, remarkable anti-inflammatory effect has not been shown. From this fact, it can be considered that in the seed of Milk Thistle, other than flavonoids etc., low molecular weight substances which show extremely excellent anti-inflammatory effect are present In inactive form and the materials are activated by applying heating treatment with far Infrared rays and brewing treatment.

EXAMPLES

In the following, anti-inflammatory effect of Milk Thistle seed is described in detail.

Example 1

Experiment on human white blood cell

White blood cells (neutrophile and lymphocyte) were collected from peripheral blood of healthy man and charged in a test tube, and untreated Milk Thistle seed or one applied with the treatments of the present invention was added thereto. Then, effects were examined with respect to five points which are considered to be promoting factors of inflammation, i.e. (1) calcium ion concentration in neutrophile, (2) migration ability of neutrophile, (3) englobement ability of neutrophile, (4) production of active oxygen ($0-0^-$) by neutrophile, and (5) reactivity of lymphocyte to phytohaemagglutinin (PHA) (blastomogenous phenomenon).

[Experimental methods]

(1) Calcium ion concentration in neutrophile

Peripheral venous blood was collected, and neutrophiles and lymphocytes were separated and obtained by using Ficoll Hypaque. In 2 ml of KRP containing 0.1 mM (millimole) of calcium chloride were suspended $10^7$ cell/ml of neutrophiles, 0.1 μM of Fura-2 A/M was added thereto and the mixture was slowly shaked at 37° C. for 30 minutes. Next, the mixture was washed twice with KRP, 15 μl of $10^{-6}$M fMLP was added thereto and calcium ion concentration was measured by using spectrophotofluorometer F-4000 (trade name, Hitachi Ltd.).

(2) Migration ability of neutrophile

An agar plate was prepared by mixing 2.5 ml of RPMI added with 10 % of deactivated calf serum and 2.5 ml of 2.4 % agar solution. Then, three holes having a diameter of 3 mm were made at intervals of 8 mm from the center to the outside. In the center hole, 10 μl of RPMI 1640 solution suspended with $10^6$ cells/ml of neutrophiles was placed; in the middle hole, 10 μl of PRMI 1640 solution was placed as a control, and in the outside hole, 10 μl of $10^{-6}$M fMLP was placed as a migration stimulating agent. Next, after this agar plate was allowed to stand at 37° C. for 2 hours, the distance of the neutrophiles in the center hole moved toward the outside hole was measured and it was represented as migration ability of neutrophiles.

(3) Englobement ability of neutrophile 0.1 ml of paraffin oil which was opsonized by human serum was collected and added to 0.9 ml of KRP solution to which $2 \times 10^7$ cells of neutrophiles were added, and the mixture was allowed to stand at 37° C. for 5 minutes. Then, ice-cooled KRP was added to the mixture to stop the reaction, and the surfaces of neurophiles were washed three times well to remove paraffin oil adhered to the surfaces of neutrophiles. Subsequently, paraffin oil drops englobed by neutrophile were extracted with a mixture of chloroform/methanol (1:2) and measured by a spectrophotometer (absorbance: 525 nm).

(4) Production of active oxygen ($0-0^-$) by neutrophile

In 2 ml of KRP solution containing 5 mM of glucose and 1 mg/ml of gelatin, were suspended $10^6$ cells of neurophiles, and the mixture was allowed to stand at 37° C. for 5 minutes. Then, 0.1 mM of ferricytochrome C and 1 mg/ml of opsonized zymozan were added thereto and the mixture was allowed to stand at 37° C. for 5 minutes. Next, 0.1 ml of the supernatant was collected, and this was added to 2 ml of 100 mM potassium phosphate solution (pH 7.8) containing 0.1 mM of EDTA, and the reduction degree of active oxygen which reduces cytochrome C was measured by a spectrophotometer (absorbance: 550 nm) with two wavelengths to counter an amount of the active oxygen. (5) Reactivity of lymphocyte to phytohaemagglutinin (blastomogenous phenomenon)

To 2 ml of RPMI 1640 solution containing 20% of deactivated calf serum and $2 \times 10^5$ cells of monocytes treated with mitomycin, were suspended $3 \times 10^6$ cells of lymphocytes. Then, 10 μg/ml of PHA was added thereto and the mixture was allowed to stand at 37° C. for 3 days. 24 hours before completion of the reaction, 2 Ci/mM of [$^3$H] was added and an amount of [$^3$H] taken by the lymphocytes within the final 24 hours was measured.

[Experiment]

Seeds of Milk Thistle to which far infrared rays heating and brewing treatments were applied according to the present invention and untreated seeds of Milk Thistle were powdered, respectively, and each 1.6 mg/ml of them was sonicated by ultrasonic wave. Then, they are added to measurement systems of five kinds of inflammation factors, i.e. calcium ion concentration, migration ability, englobement ability and production of active oxygen of neutrophile, and reactivity of lymphocyte to PHA, and then, effects to the measured values were examined.

Further, as comparative pharmaceuticals, 1.6 mg/ml of antioxidant composition disclosed in Japanese Patent Application Laid-Open No. 63-79834 and each $10^{-4}$ M of commercially available anti-inflammatory agents, Rinderon (adrenocortlcal hormone, betamethasone sold by Shionogi Seiyaku), Pontal (mefenamic acid sold by Sankyo), Voltaren (diclofenac sodium sold by Ciba-Geigy Corporation) and Brufen (ibuprofen sold by Kaken Seiyaku) were added to the above measurement systems of five kinds of inflammation factors, and effects to the measured values were also examined.

The experimental results are shown in Table 1.

TABLE 1

Effects of Milk Thistle and other pharmaceuticals on white blood cells

| | Neutrophile | | | | Lymphocyte |
|---|---|---|---|---|---|
| | Calcium ion concentration | Migration ability | Englobement | Active oxygen production | PHA blastomogenic |
| Milk Thistle (heated and brewed) | 47.5 (%) | 50.6 (%) | 41.6 (%) | 51.8 (%) | 47.7 (%) |
| Milk Thistle (untreated) | 72.3 | 76.1 | 69.1 | 74.8 | 70.2 |
| Antioxidant composition | 89.5 | 91.5 | 92.1 | 60.4 | 90.4 |
| Rinderon | 52.9 | 54.9 | 59.4 | 68.7 | 54.4 |

TABLE 1-continued

Effects of Milk Thistle and other pharmaceuticals on white blood cells

|  | Neutrophile | | | | Lymphocyte PHA blastomogenic |
|---|---|---|---|---|---|
|  | Calcium ion concentration | Migration ability | Englobement | Active oxygen production | |
| Pontal | 82.5 | 86.0 | 85.4 | 82.8 | 82.2 |
| Voltaren | 84.9 | 86.8 | 86.3 | 86.9 | 84.6 |
| Brufen | 87.1 | 87.7 | 87.9 | 89.0 | 88.1 |
| Control(*) | 100.0 (618 nM) | 100.0 (16.8 mm) | 100.0 (0.031 OD) | 100.0 (1.94 nM/ $10^6$ cells/min) | 100.0 (33.456 × $10^3$ CPM) |

Numerals in each row show percent values based on the control(*) values respectively.
Control (*) shows the values of inflammation factors when no pharmaceutical is added.
Numerals in the blancket of the row of Control (*) show real values of the inflammation factors.

As clearly seen from Table 1, among the comparative pharmaceuticals, the antioxidant composition markedly lowered active oxygen (O—O$^-$) which is one of the potent inflammation factors, but provided substantially no effect against the other four kinds of inflammation factors. Also, the commercially available anti-inflammatory agents other than Rinderon provided only slight inhibition effect to some of the five kinds of inflammation factors.

On the other hand, it can be understood that the seed of Milk Thistle heated with far infrared rays and brewed showed potent anti-inflammation effects, and inhibited and lowered the five kinds of inflammation factors more potently than Rinderon which is an adrenocortical hormone and is notorious as having side effects.

Also, the untreated seed of Milk Thistle inhibited and lowered five kinds of inflammation factors significantly, but the degrees thereof were weak in comparison with one to which far infrared rays heating and brewing treatments were applied.

Example 2

To total 39 cases of the so-called refractory disease patients including 10 cases of chronic articular rheumatism patients, 8 cases of progressive systemic sclerosis or dermatomyositis patients, 6 cases of systemic lupus erythematosus, 6 cases of Crohn's disease, 5 cases of Behcet's disease, and 4 cases of ulcerative colitis, which were resistive to treatments by using the antioxidant composition, the easily absorbable crude drug described in Japanese Patent Application Laid-Open No. 64-85919, adrenocortical hormone agent, etc., were administered orally 9 g/day (three times per day) of powder of Milk Thistle seed to which far infrared rays heating and brewing treatments were applied and 9 g/day (three times per day) of powder of untreated Milk Thistle seed for each 4 weeks to judge the effects whereby the results shown in Table 2 were obtained.

TABLE 2

Effects of heating and brewing treated and untreated Milk Thistles on refractory disease patients

|  |  | Total cases | Effects | | | | | Effective rate (%) |
|---|---|---|---|---|---|---|---|---|
|  |  |  | Remarkably effective | Effective | Slightly effective | No change | Not effective |  |
| Milk Thistle heated and brewed | Chronic rheumatism | 10 | 5 | 2 | 1 | 1 | 1 | 80 |
|  | Progressive systemic sclerosis, or Dermatomyositis | 8 | 3 | 2 | 1 | 1 | 1 | 75 |
|  | Systemic lupus erythematosus | 6 | 2 | 2 | 1 | 0 | 1 | 83 |
|  | Crohn's disease | 6 | 2 | 2 | 0 | 1 | 1 | 66 |
|  | Behcet's disease | 5 | 1 | 2 | 1 | 0 | 1 | 80 |
|  | Ulcerative colitis | 4 | 1 | 1 | 1 | 1 | 0 | 75 |
| Milk Thistle Untreated | Chronic rheumatism | 10 | 0 | 1 | 2 | 3 | 4 | 30 |
|  | Progressive systemic sclerosis, or Dermatomyositis | 8 | 0 | 1 | 1 | 2 | 4 | 25 |
|  | Systemic lupus erythematosus | 6 | 0 | 1 | 0 | 1 | 4 | 16 |
|  | Crohn's disease | 6 | 0 | 1 | 1 | 1 | 3 | 33 |
|  | Behcet's disease | 5 | 0 | 1 | 0 | 1 | 3 | 20 |
|  | Ulcerative colitis | 4 | 0 | 0 | 1 | 1 | 2 | 25 |

"No change" means the same effect as in the case of using adrenocortical hormone, neither improvement nor worsening being observed as compared with use of adrenocortical hormone.
"Not effective" means that the disease became worse than in the case of using adrenocortical hormone.
"Effective rate" shows a percentage of remarkably effective, effective and slightly effective in the total cases.

As clearly seen from Table 2, Milk Thistle seed heated with far infrared rays and brewed was effective on 66–83% of the refractory disease patients who took it orally.

As a result, many chronic articular rheumatism patients who had walked by using a stick or a walker can walk by themselves. In four patients who had been in last stage of progressive systemic sclerosis or dermatomyositis having lung sclerosis confirmed by pectoral X-P observation and remarkable dyspnea, dyspnea was improved and disappearance was confirmed by pectoral X-P observation in all the cases.

Also, among 7 cases in total of Crohn's disease patients, Behcet's disease patients (intestinal tube type) and ulcerative colitis patients, whose intestinal tubes had been operated many times, 5 cases became of no need to effect operation of intestinal tube, and go on well thereafter.

On the other hand, effects of untreated Milk Thistle seed were substantially same as those of the commercially available anti-inflammatory agents (except for the adrenocortical hormone agent) and inferior to those of the adrenocortical hormone agent, and far inferior to those of seed heated with far infrared rays and brewed. In particular, untreated Milk Thistle seed was not effective for any case resistive to adrenocortical hormone agent or antioxidant composition.

Example 3

To 61 cases in total of new patients of the aforesaid refractory diseases (29 cases of chronic articular rheumatism, 10 cases of progressive systemic sclerosis or dermatomyositis, 8 cases of systemic lupus erythematosus, 6 cases of Crohn's disease, 6 cases of Behcet's disease (intestinal tube type) and 2 cases of ulcerative colitis), were administered orally 9 g/day (separately administered three times per day) of powder of Milk Thistle seed heated with far infrared rays and brewed, 9 g/day (separately administered three times per day) of powder of untreated Milk Thistle seed, 9 g/day (separately administered three times per day) of the antioxidant composition, Rinderon (0.5 mg×3 tablets/day), Pontal (250 mg×4 tablets/day), Voltaren (25 mg×3 tablets/day) and Brufen (200 mg×6 tablets/day) for each 4 weeks to judge the effects thereof whereby the results shown in Table 3 were obtained.

In this example, all drugs are not successively administered to all the patients for every 4 weeks. Further, only in a part of cases, the same pharmaceutical is administered orally to the all patients of the same disease. Also, in a part of the cases, a certain pharmaceutical is administered for 4 weeks, and thereafter the other pharmaceutical is administered for 4 weeks.

TABLE 3

Effects of Milk Thistle and commercially available anti-inflammatory agents on refractory disease patients

| | total cases | Remarkably effective | Effective | Slightly effective | No change | Not effective | Effective rate (%) |
|---|---|---|---|---|---|---|---|
| Milk Thistle (heated & brewed) | 10 | 4 | 2 | 2 | 1 | 1 | 80 |
| Milk Thistle (untreated) | 8 | 0 | 1 | 1 | 2 | 4 | 25 |
| Antioxidant composition | 21 | 2 | 3 | 4 | 7 | 5 | 42 |
| Rinderon | 10 | 2 | 2 | 1 | 2 | 3 | 50 |
| Pontal | 11 | 0 | 0 | 2 | 1 | 8 | 18 |
| Voltaren | 13 | 0 | 0 | 2 | 2 | 9 | 15 |
| Brufen | 14 | 0 | 0 | 1 | 2 | 11 | 7 |

As clearly seen from Table 3, remarkably effective and effective cases are most revealed in Milk Thistle seed heated with far infrared rays and brewed, and adrenocortical hormone (Rinderon) followed thereto. Other pharmaceuticals showed a little effect and untreated Milk Thistle seed showed substantially same effect as the commercially available anti-inflammatory agents.

Example 4

To 56 cases in total of general inflammation disease patients (16 cases of lumbago, 10 cases of myalgia, 9 cases of shoulder stiffness 10 cases of bruise, and 11 cases of cold constitution), were administered orally the same pharmaceuticals in same doses as in Example 3 for 4 weeks and the effects thereof were judged. The results are shown in Table 4.

TABLE 4

Effects of Milk Thistle and commercially available anti-inflammatory agents on general Inflammation patients

| | total cases | Effects | | | | | Effective rate (%) |
| --- | --- | --- | --- | --- | --- | --- | --- |
| | | Remarkably effective | Effective | Slightly effective | No change | Not effective | |
| Milk Thistle (heated & brewed) | 12 | 3 | 4 | 2 | 2 | 1 | 75 |
| Milk Thistle (untreated) | 11 | 0 | 2 | 2 | 2 | 5 | 36 |
| Antioxidant composition | 14 | 1 | 2 | 2 | 5 | 4 | 35 |
| Rinderon | 13 | 2 | 2 | 4 | 2 | 3 | 61 |
| Pontal | 15 | 1 | 2 | 4 | 4 | 4 | 46 |
| Voltaren | 17 | 1 | 3 | 2 | 5 | 6 | 35 |
| Brufen | 15 | 0 | 2 | 2 | 5 | 6 | 26 |

As clearly seen from Table 4, the results are substantially same as in above Example 3, but the difference between Milk Thistle seed heated with far infrared rays and brewed and the other pharmaceuticals was not clearer than that of Example 3.

As clearly seen from the result in Example 1, the seed of Milk Thistle to which far infrared rays heating and brewing treatments are applied is remarkably inhibitive as compared to those of untreated ones, in each of calcium ion concentration, migration ability, englobement ability and active oxygen production of neutrophile, and reactivity of lymphocyte to PHA which are white blood cell inflammation factors.

Also, with regard to the respective inhibiting effects against the above respective inflammation factors, the composition of the present invention is far excellent than the effects of the antioxidant composition described in Japanese Patent Application Laid-Open No. 63-79834 or commercially available anti-inflammatory agents.

As clearly seen from the respective results in Examples 2, 3 and 4, the seed of Milk Thistle heated with far infrared rays and brewed showed marked effects against not only general inflammation disease such as lumbago, muscular pain, shoulder stiffness, bruise and cold constitution, but also chronic articular rheumatism.

Also, it showed marked effects against refractory diseases, i.e. specific diseases designated by the Ministry of Health and Welfare of Japan such as progressive systemic sclerosis, dermatomyositis, systemic lupus erythematosus, Crohn's disease, Behcet's disease and ulcerative colitis. Further, it even showed marked effects on cases where the use of adrenocortical hormones produced no effects. Thus, far infrared ray heated and brewed seeds of Milk Thistle are novel anti-inflammatory agents and are beneficial by being widely available for use.

What is claimed is:

1. A method of preparing an anti-inflammatory composition which consists of the steps:

heating seed of milk thistle by far-infrared rays for the cleaving of polymers of components that are found in seed of milk thistle at a temperature near to but not exceeding 100° C. for ½ to 2 hours; and brewing the heated seed of milk thistle with brewing material selected from the group consisting of brewing bacteria, digestive enzyme and protein hydrolyze, whereby an orally administrable anti-inflammatory composition is provided without any oil added, an anti-inflammatory activity of the composition being significantly higher than that seen with untreated seed of milk thistle.

2. The method according to claim 1 wherein the heating step is carried out by far-infrared rays with a wavelength of 4 to 14 μm.

3. The method according to claim 1 wherein the heating step is carried out in a vessel made of a ceramic coated metal or pottery material.

4. The method according to claim 1 wherein the brewing step is carried out in the presence of Koji fungus.

5. The method according to claim 1 wherein the brewing step is carried out at a temperature of 27° to 35 °C. for 3 to 7 days.

* * * * *